United States Patent [19]

Lomen

[11] Patent Number: 4,489,080

[45] Date of Patent: Dec. 18, 1984

[54] PROCESS FOR ANALGESIC TREATMENT

[75] Inventor: Pavel L. Lomen, Plainwell, Mich.

[73] Assignee: The Upjohn Company, Kalamazoo, Mich.

[21] Appl. No.: 447,051

[22] Filed: Dec. 6, 1982

Related U.S. Application Data

[63] Continuation of Ser. No. 277,557, Jul. 26, 1981, abandoned.

[51] Int. Cl.³ .................. A61K 31/19; A61K 31/135; A61K 31/445/31/485
[52] U.S. Cl. .................................. 424/260; 424/267; 424/317; 424/330
[58] Field of Search ................ 424/260, 317, 267, 330

[56] References Cited

PUBLICATIONS

Chem. Abst., vol. 90-33960z (1979).
S. A. Cooper, et al., "Relative Efficacy of an Ibuprofen–Codeine Combination", Clin. Pharmacol. Ther. 27(2), 1980, p. 249.

*Primary Examiner*—Stanley J. Friedman
*Attorney, Agent, or Firm*—William G. Jameson; John J. Killinger

[57] ABSTRACT

An improved process for the management of pain by concommittant administration of narcotic analgesics and flurbiprofen or salt or ester thereof. Process for reducing dosage and dosage forms are disclosed.

10 Claims, No Drawings

PROCESS FOR ANALGESIC TREATMENT

This is a continuation of application Ser. No. 277,557, filed July 26, 1981, now abandoned.

BRIEF DESCRIPTION OF THE INVENTION

This invention is an improvement in the management of pain by the administration of narcotic analgesics comprising the step of concomittant administration of flurbiprofen, 3-fluoro-4-phenylhydratropic acid, or a pharmacologically acceptable salt or ester thereof and combinations of the above in unit dosage form.

BACKGROUND OF THE INVENTION

Narcotic analgesics have been used for the relief of moderate to severe pain. Severe pain, particularly, has required the use of narcotic analgesics in large and increasing dosage amounts.

A disadvantage of the narcotic analgesic is the development of dependence or addiction and tolerance to their action. Further, adverse reactions to large doses are respiratory and circulatory depression.

Flurbiprofen, a non-steroidal anti-inflammatory drug, (NSAID) has been used in rheumatic and degenerative diseases of the joints and for reducing platelet adhesiveness.

DETAILED DESCRIPTION OF THE INVENTION

This invention is a synergistic combination of known drugs useful in the management of moderate to severe pain. The synergistic combination is a narcotic analgesic and flurbiprofen or a salt or ester thereof.

The narcotic analgesics of the present invention are the naturally occurring opium alkaloids, semi-synthetic and synthetic derivatives. They can be, for example, morphine, hydromorphone, oxymorphone levorphanol, methadone, meperidine, anileridine, alphaprodine, fentanol, or codeine.

The narcotic analgesics are combined for synergistic advantages with flurbiprofen (3-fluoro-4-phenylhydratropic acid) or a pharmacologically acceptable salt or ester thereof. The pharmacologically acceptable salts can be, for example, the alkali metal, alkaline earth or ammonium salts. Esters can be the alkyl ester of from one to eight carbon atoms, inclusive, including the isomeric forms thereof.

The synergistic action of the two ingredients of the present invention results in better control of pain while delaying or eliminating narcotic dependance and resistance.

The dosage amount initially is the usual dosage amount for the narcotic analgesic and about 50 mg of flurbiprofen four or five times a day. After two days of administering the combination, the dose amount of narcotic analgesic is gradually lowered over a period of fourteen days to the lowest acceptable amount of narcotic to maintain analgesia from the combination. After fourteen days when the lowest narcotic amount is determined, the amount of flurbiprofen is lowered to 100–200 mg/day to maintain the same control of pain.

The narcotic analgesic and flurbiprofen can be administered in the same dosage unit or can be prepared in separate dosage units and the dosage units administered at the same time. Different forms of dosage units can be used, i.e., a tablet of flurbiprofen and an injection of narcotic.

The compositions of the present invention are preferably presented for systemic administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of the synergistic combination of active ingredients.

For oral administration either solid or fluid unit dosage forms can be prepared.

Powders are prepared quite simply by comminuting the active ingredients to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture and filling into formed gelatin sheaths. Advantageously, as an adjuvant to the filling operation, lubricant such as talc magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing the active ingredients, suitably comminuted, with a diluent or base such as starch lactose, kaolin, dicalcium phosphate and the like. The powder mixture can be granulated by wetting with a binder such as corn syrup, gelating solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearate salt, talc or mineral oil. The lubricated mixture is then compressed into tablets.

Advantageously, the tablet can be provided with a protective coating consisting of a sealing coat or enteric coat of shellac, a coating of sugar and methylcellulose and a polish coating of carnauba wax.

Fluid unit dosage forms for oral administration such as syrups, elixirs and suspensions can be prepared wherein each teaspoonful of composition contains a predetermined amount of the active ingredients for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing the active ingredients and a sterile vehicle, water being preferred. The active ingredients, depending on the form and concentration used, can be either suspended or dissolved in the vehicle. In preparing solutions the water-soluble active ingredients can be dissolved in water for injection and filter sterilized before filling into a suitable vial or ampule and sealing. Advantageously, adjuvants such as a local anesthetic, preservative and buffering agents can be dissolved in the vehicle. Cosolvents such as ethanol or propylene glycol can be used in the solvent system. Parenteral suspensions are prepared in substantially the same manner except that the active ingredients are suspended in the vehicle instead of being dissolved and sterilization cannot be accomplished by filtration. The active ingredients can be sterilized by exposure to ethylene oxide before suspending in the sterile vehicle. Advantageously, a surfactant or wetting agent is included in the composition to facilitate uniform distribution of the active ingredients.

In addition to oral and parenteral administration, the rectal and vaginal routes can be utilized. Active ingredients can be aadministered by means of a suppository. A vehicle which has a melting point at about body temperature or one that is readily soluble can be utilized. For example, cocoa butter and various polyethylene glycols (carbowaxes) can serve as the vehicle.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specification for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosages forms in accord with this invention are tablets, capsules, troches, suppositories, powder packets, wafers, cachets, teaspoonfuls, tablespoonfuls, dropperfuls, ampules, vials, segregated multiples of any of the foregoing and other forms as herein described.

The following examples are illustrative of the present invention, but are not intended to be limiting.

EXAMPLE 1

Hard Gelatin Capsules

One thousand two-piece hard gelatin capsules for oral use, each capsule containing 50 mg of flurbiprofen and 15 mg morphine sulfate are prepared from the following types and amounts of ingredients:

| Flurbiprofen | 50 gm |
| Morphine sulfate | 15 gm |
| Lactose | 100 gm |
| Corn starch | 20 gm |
| Talc | 20 gm |
| Magnesium stearate | 2 gm |

The flurbiprofen and morphine sulfate finely divided by means of an air micronizer, are added to the other finely powdered ingredients, mixed thoroughly and then encapsulated in the usual manner.

The foregoing capsules are useful for preventing pain following laparotomy by the oral administration of one capsule four times a day.

Using the procedure above, capsules are similarly prepared containing morphine sulfate in 7.5 and 3.75 mg amounts by substituting 7.5 and 3.75 gm of morphine sulfate for the 15 gm used above. These capsules are used to reduce the narcotic dose of the preceeding examples.

EXAMPLE 2

Soft Gelatin Capsules

One-piece soft gelatin capsules for oral use, each containing 50 mg of flurbiprofen and 15 mg of morphine sulfate (finely divided by means of an air micronizer) are prepared by first suspending the compounds in 0.5 ml of corn oil to render the material capsulatable and then capsulating in the above manner.

The foregoing capsules are useful for preventing pain following caesarian section by the oral administration of one capsule four times a day.

EXAMPLE 3

Tablets

One thousand tablets, each containing 50 mg of flurbiprofen and 15 mg morphine sulfate are prepared from the following types and amounts of ingredients:

| Flurbiprofen micronized | 50 gm |
| Morphine sulfate | 15 gm |
| Lactose | 75 gm |
| Corn starch | 50 gm |
| Magnesium stearate | 4 gm |
| Light liquid petrolatum | 5 gm |

The flurbiprofen and morphine sulfate (finely divided by means of an air micronizer) are added to the other ingredients and then thoroughly mixed and slugged. The slugs are broken down by forcing then through a number sixteen screen. The resulting granules are then compressed into tablets, each tablet containing 50 mg of flurbiprofen and 15 mg of morphine sulfate.

The foregoing tablets are useful for preventing pain following a broken femur by the oral administration of one tablet four times a day, for two days following setting the bone.

Using the procedure above, tablets are similarly prepared containing morphine sulfate in 7.5 mg and 3.75 mg amounts by substituting 7.5 gm and 3.75 gm of morphine sulfate for the 15 gm used above. These tablets are used to reduce the narcotic dose of the preceeding examples.

EXAMPLE 4

Oral Suspension

One thousand ml of an aqueous suspension for oral use, containing in each teaspoonful (5 ml) dose, 100 mg of flurbiprofen aluminum salt is prepared from the following types and amounts of ingredients:

| Flurbiprofen, aluminum salt micronized | 20 gm |
| Citric acid | 2 gm |
| Benzoic acid | 1 gm |
| Sucrose | 700 gm |
| Tragacanth | 5 gm |
| Lemon oil | 2 gm |
| Deionized water, q.s. | 1000 ml |

The citric acid, benzoic acid, sucrose, tragacanth and lemon oil are dispersed in sufficient water to make 850 ml of suspension. The flurbiprofen aluminum salt (finely divided by means of an air micronizer) is stirred into the syrup until uniformly distributed. Sufficient water is added to make 1000 ml.

The composition so prepared is useful for preventing pain of cancer of the bowels at a dose of one tablespoonful (15 ml) four times a day with ¼ gram of morphine sulfate given I.M. four times a day.

EXAMPLE 5

A sterile aqueous solution for parenteral (i.v.) injection, containing in one liter, 350 mg of flurbiprofen, sodium salt is prepared from the following types and amounts of ingredients:

| | |
|---|---|
| Flurbiprofen sodium salt | 350 mg |
| Water for injection, q.s. | 1000 ml |

To the sterile solution is added sterilized flurbiprofen, sodium salt and filled into sterile containers sealed.

The composition so prepared is useful for preventing pain of inoperable cancer at a dose of one liter every eight hours with ½ grain of morphine sulfate every eight hours.

EXAMPLE 6

Following the procedure of the proceeding Examples 1 through 5, inclusive, compositions are similarly prepared substituting equimolar amounts of the ester, e.g., methyl, ethyl, isopropyl, octyl or salts, e.g., sodium, potassium, ammonium, for the compound of the examples.

EXAMPLE 7

Following the procedure of the preceeding Examples 1 through 5, inclusive, a dosage unit and regimen is similarly followed substituting an equi-analgesic amount each of: hydromorphine, oxymorphone, levorphanol, methandone, meperidine, alphapradine, fentanol, or codeine for the morphine of the examples.

I claim:

1. In the process of treating pain by the systemic administration of analgetic amounts of narcotic analgesics the improvement comprising the step of concomitant systemic administration of an analgetic amount of 3-fluro-4-phenylhydratropic acid or an alkyl ester of from one to eight carbon atoms, inclusive, or a pharmacologically acceptable salt, thereof.

2. A process for treating moderate to severe pain in humans comprising the concomitant systemic administration of an analgetic amount of a narcotic analgesic and an analgetic amount of 3-fluoro-4-phenylhydratropic acid or an alkyl ester of from one to eight carbon atoms, inclusive, or a pharmacologically acceptable salt, thereof.

3. An analgesic composition, in unit dosage form, comprising a synergistic analgetic amount of a narcotic analgesic and 3-fluoro-4-phenylhydratropic acid or an alkyl ester of from one to eight carbon atoms, inclusive, or a pharmacologically acceptable salt, thereof.

4. The process of claim 1 wherein the narcotic analgesic is selected from the group consisting of morphine, hydromorphone, oxymorphone, levorphanol, methadone, meperidine, anileridine, alphaprodine, fentanol, or codeine.

5. The process of claim 1 wherein the narcotic analgesic is selected from the group consisting of morphine, hydromorphone, oxymorphone or codeine.

6. The process of claim 2 wherein the narcotic analgesic is selected from the group consisting of morphine, hydromorphone, oxymorphone, levorphanol, methadone, meperidine, anileridine, alphaprodine, fentanol, or codeine.

7. The process of claim 2 wherein the narcotic analgesic is selected from the group consisting of morphine, hydromorphone, oxymorphone or codeine.

8. The composition of claim 3 wherein the narcotic analgesic is selected from the group consisting of morphine, hydromorphine, oxymorphone, levorphanol, methadone, meperidine, anileridine, alphaprodine, fentanol, or codeine.

9. The composition of claim 3 wherein the narcotic analgesic is selected from the group consisting of morphine, hydromorphone, oxymorphone or codeine.

10. The composition of claim 3 wherein the narcotic analgesic is codeine.

* * * * *